United States Patent [19]
Quick et al.

[11] 3,976,073
[45] Aug. 24, 1976

[54] VIAL AND SYRINGE CONNECTOR ASSEMBLY

[75] Inventors: John L. Quick, Buffalo Grove; Daniel D. Wyncott, Arlington Heights, both of Ill.

[73] Assignee: Baxter Laboratories, Inc., Deerfield, Ill.

[22] Filed: May 1, 1974

[21] Appl. No.: 465,988

[52] U.S. Cl. .......................... 128/272; 128/214 C; 128/214 D; 128/DIG. 24; 128/DIG. 28; 128/218 N
[51] Int. Cl.² ............................................ A61J 5/00
[58] Field of Search ............... 128/220, 272, 214 R, 128/214 D, 216, 218 M, 218 NV, 214 C, 221, 218 D, 218 DA, 218 R, 218 N, DIG. 28, DIG. 24, DIG. 5; 222/80–82, 83.5, 86; 141/25–28

[56] References Cited
UNITED STATES PATENTS

| 2,735,430 | 2/1956 | Huber .......................... 128/218 NV |
| 2,904,043 | 9/1959 | Friedman ........................ 128/218 D |
| 2,955,595 | 10/1960 | Semple ............................... 128/2 F |
| 3,110,309 | 11/1963 | Higgins .......................... 128/218 D |
| 3,150,661 | 9/1964 | Maki ........................... 128/218 NV |
| 3,336,924 | 8/1967 | Sarnoff et al. ...................... 128/272 |
| 3,470,867 | 10/1969 | Goldsmith...................... 128/221 X |
| 3,542,023 | 11/1970 | Ogle ............................... 128/218 R |
| 3,659,602 | 5/1972 | Cloyd................................ 128/220 |
| 3,783,997 | 1/1974 | Brown............................ 128/218 D |
| 3,826,261 | 7/1974 | Killinger ........................... 128/272 |
| 3,828,779 | 8/1974 | Ogle................................... 128/272 |

FOREIGN PATENTS OR APPLICATIONS

| 1,373,027 | 8/1964 | France ........................... 128/214 C |
| 115,391 | 6/1929 | Germany ......................... 128/272 |

*Primary Examiner*—Robert W. Michell
*Assistant Examiner*—Henry J. Recla
*Attorney, Agent, or Firm*—Louis Altman; Garrettson Ellis; Paul C. Flattery

[57] ABSTRACT

A vial and syringe connector assembly is provided for the sterile addition of fluid material to a sealed container having an injection-type access port. The assembly comprises a syringe connector which carries a hollow, injection needle having one pointed end for passing through such access port. The other needle end is blunt. An open mouthed vial for the fluid material has an elastomeric sealing piston disposed in the vial mouth and movable in sealing relation axially of the vial. A bore is also defined axially in the sealing piston of a size to receive the blunt end of the needle. An elastomeric diaphragm which is integral with the sealing piston occludes the bore. The vial and sealing piston are carried on the syringe connector with the blunt needle end positioned in the bore. The blunt needle end is used to rupture the diaphragm for fluid flow through the needle of the contents of the vial without accidental "coring" of the diaphragm and consequent obstruction of flow through the needle.

2 Claims, 4 Drawing Figures

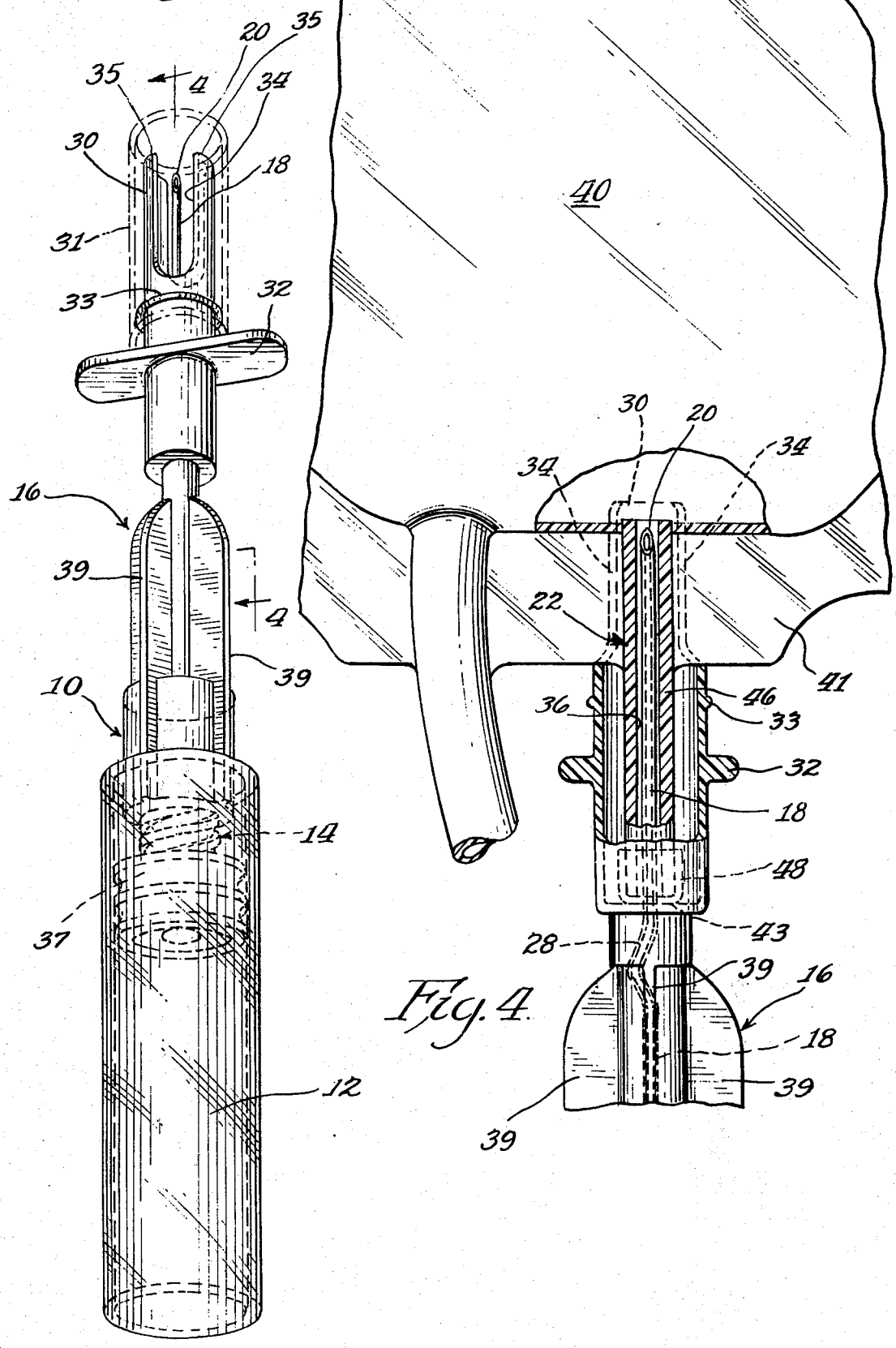

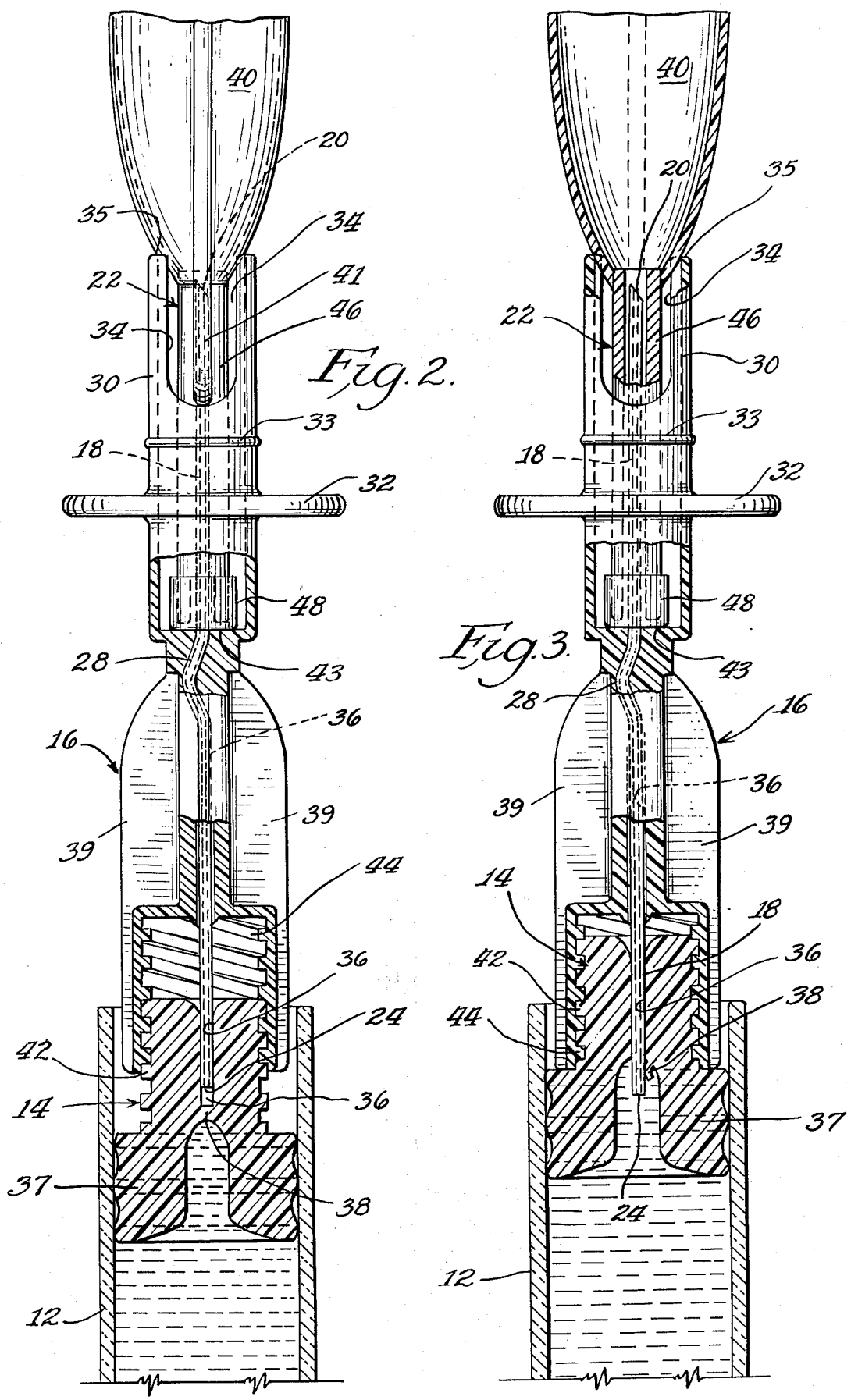

VIAL AND SYRINGE CONNECTOR ASSEMBLY

BACKGROUND OF THE INVENTION

This invention relates to an improvement in sterile syringe injection devices, in which a vial having an elastomeric sealing piston mounted therein is carried by an improved syringe connector, to provide sterile access to the contents of the vial for its transfer in sterile manner into a parenteral solution container, solution administration set, or the like, which has a projecting, resealable injection site.

Representative prior art structures which can be used for a similar purpose are disclosed in U.S. Pat. Nos. 2,371,086; 3,376,866; and 3,378,008. In each of these patents, as well as other patents and publications, a sterile vial is provided in conjunction with a syringe connector assembly having a hollow injection needle exposed at both ends. One end of the injection needle penetrates the closure of the vial, while the other end of the needle is used for injection.

This type of system finds particular use in the area of adding supplemental medication to parenteral solution containers. The supplemental medication, which may be potassium chloride solution or other medicament as required by a patient, can be added to a parenteral solution container, such as a VIAFLEX parenteral solution bag of the type sold by Travenol Laboratories, Inc., by penetrating the closure member of the parenteral solution container by one end of the injection needle, and then penetrating the vial of medicament with the other end of the needle, followed by slowly sliding an elastomeric sealing piston associated with the vial into the vial, to cause the medicament solution to be expelled through the injection needle.

However, the many designs of the cited prior art have several drawbacks.

First, in the prior art such as U.S. Pat. No. 3,378,008, when the rear end of the injection needle is forced through the elastomeric sealing piston of the vial, the needle may accidentally cut a small core of rubber from the sealing diaphragm of the sealing piston as it advances. This core may enter and remain in the bore of the needle, restricting or completely blocking the flow of the contents of the vial through the needle, or pass into the container into which an injection is being made.

Second, in similar prior art, the front needle ends of the prior art vial and syringe connector assemblies are inconveniently and dangerously exposed, to prick fingers during use, and to pick up contamination. Also, the needle can be advanced through the injection site in a direction not quite axial to it, which may cause the needle to penetrate a wall of plastic parenteral solution bag, which in turn may cause a leak and spoil sterility. In this event, both the parenteral solution bag, and the vial and syringe connector assembly, may have to be discarded and the whole preparation process begun again with new equipment.

However, when a needle has a protective sleeve, it has been found with respect to parenteral solution bags that many auxiliary medicament solutions ineffectively mix with the parenteral solution in a bag. This problem becomes more severe as the density of the medicament solution increases. For example, potassium chloride, due to its high density will often not mix satisfactorily with the parenteral solution unless the injection needle of the connector assembly can penetrate farther into the parenteral solution container (via the injection site) than is possible with a needle surrounded by a simple sleeve, of the type currently offered for sale.

In accordance with this invention, means are provided to eliminate these drawbacks, separately or in combination as desired.

DESCRIPTION OF THE INVENTION

In accordance with this invention, there is provided an improved vial and syringe connector assembly for the sterile addition of fluid material to a sealed container having an injection-type access port or site. The assembly comprises a novel syringe connector which carries a hollow injection needle having one pointed end for passing through such an access port, and another, blunt end for rupture of a diaphragm integral with an elastomeric sealing piston, in a manner which reduces the danger of "coring"; that is, the cutting of a core out of the diaphragm by the needle, in which the core remains in the hollow lumen of the needle, thus obstructing flow. The needle is secured to the syringe connector at an area between the needle ends.

An open mouthed vial for containing the fluid material to be injected is provided, having an elastomeric sealing piston disposed in the vial mouth, but movable in sealing relation axially with respect to the vial. A bore is defined in the sealing piston of a size to snugly and sealingly receive the blunt end of the injection needle. The diaphragm mentioned above occludes the bore, and is integral with the sealing piston, being preferably located adjacent the inner end of the sealing piston bore relative to the vial.

Carrying means are provided for holding the vial and sealing piston in such a position that the blunt end of the needle is positioned in the bore. More specifically, the syringe connector and sealing piston both define mating helical thread and groove means, or another structure having equivalent function, to permit axial motion of the needle in the bore to permit the blunt needle end to rupture the diaphragm for fluid flow through the needle without the danger of coring, when such access to the contents of the vial is desired.

It is a further advantage of this invention for the syringe connector to define a sleeve positioned axially and in spaced relation about the pointed end of the needle, so that the pointed needle end is recessed within the sleeve. Accordingly, the sleeve serves as a positioning guide as the pointed end penetrates an end of a tubular access port, which greatly reduces the likelihood that the pointed end of the needle will assume a skewed position to penetrate a side wall of the access port or an associated, thin-walled plastic container for parenteral solution or the like. Also, contamination of the needle by touching is prevented in a better manner, and accidental injury to the hand from the needle is likewise prevented.

Preferably, the sleeve mentioned above defines opposed axial slots, for advantageous use with a flat type, sealed container as described below.

In the drawings:

FIG. 1 is a perspective view of an improved vial and syringe connector assembly of this invention.

FIG. 2 is an elevational view, taken partly in longitudinal section, of the vial and syringe connector assembly of FIG. 1, prior to rupture of the diaphragm of the sealing piston by the blunt end of the injection needle.

FIG. 3 is a view similar to FIG. 2, taken after the blunt end of the needle has ruptured the diaphragm of the sealing piston, and showing the position of the pointed end of the injection needle after it has deeply penetrated a tubular access port of a sealed container.

FIG. 4 is an elevational view of the vicinity of the pointed needle end of the structure of FIG. 3, rotated 90° about the longitudinal axis of the vial and syringe connector assembly with respect to the view of FIG. 3.

Referring to the drawings, FIG. 1 discloses a vial and syringe connector assembly 10. Vial 12, which typically contains an auxiliary medicament such as potassium chloride solution or the like, carries in its mouth an elastomeric sealing piston 14 which is movable in sealing relation axially with the vial.

Syringe connector 16 carries a hollow injection needle 18 having one pointed end 20 for passing through an access port 22 of a parenteral solution container or the like (FIGS. 2, 3 and 4), and another, blunt end 24 (FIGS. 2 and 3) for penetrating sealing piston 14.

Syringe connector 16 is typically made of molded plastic, and which carries needle 18 at a central portion thereof, spaced from the needle ends. Needle 18 may be firmly secured to connector 16 by a retention means, which in the embodiment shown comprises an arcuate, bent or curved portion 28 in the needle about which the connector 16 is molded. This causes the needle to be firmly held by the connector 16.

Other needle securing means may also be used if desired, such as a flange mounted on the needle and secured within connector 16. Also separate, spaced front and rear needles may be used by separately attaching them to the connector, and defining a bore through the connector between the separate needles, for fluid communication between them.

A sleeve 30 is defined about the pointed end of needle 20, in spaced relation thereto, with needle end 20 recessed in the sleeve, to serve as an alignment guide as the needle is advanced into an injection site or access port of a parenteral solution container. The sleeve also reduces the possibility of contamination of the needle end, pricking of the operator's fingers, and the like. FIG. 1 shows cover 31, secured over sleeve 30, and removably held in place by detent 33 on sleeve 30.

Transverse member 32 provides the operator with a finger hold, and a surface to press against as the needle is advanced or withdrawn from the injection site, and during injection of the medication.

A pair of opposed axial slots 34, open at their front ends 35, are defined in sleeve 30 to permit deep needle penetration into a flat, sealed container as shown in FIGS. 3 and 4, and as described below. The flat edge of such a container can pass into the slots, to permit greater needle penetration.

Elastomeric sealing piston 14 is shown in FIG. 2 to define a bore 36 of a size to snugly and sealingly receive the blunt end 24 of needle 18. An elastomeric diaphragm 38, which is made integrally as a part of the sealing piston, occludes bore 36 in its preuse configuration, sealing the contents of vial 12. Diaphragm 38 is preferably positioned as shown, adjacent the inner end of bore 36.

As shown in FIG. 2, blunt end 24 of needle 18 is initially positioned within bore 36. Thus, after the connector 16 has been sterilized, needle end 24 tends to remain sterile until used, since it remains sealed within bore 36. Thus, upon use, a sterile flow path is reliably provided for solution in vial 12 to pass through needle 18.

Sealing piston 14 defines a sealing portion 39, which acts as a liquid-tight plunger or piston, so that when opened by rupturing diaphragm 38 by needle 18, and piston 14 is pushed downwardly into the vial 12, the liquid contents will be expelled from the vial. Piston 14 also defines helical thread and groove means 42, proportioned to mate with corresponding thread and groove means 44 which are carried by the syringe connector 16. This arrangement serves as a means for carrying vial 12 and sealing piston 14 in a position in bore 36. Blunt end 24 protrudes axially beyond thread and groove means 44, which forms a spaced sleeve about needle 18.

Accordingly, by relative rotation of thread and groove means 42, 44, the blunt end 24 of needle 18 can be advanced or retracted with respect to sealing piston 14. Thus, when access to the contents of vial 12 is desired, syringe connector 16 can be rotated with respect to sealing piston 14 until the blunt end 24 of the needle advances into rupturing contact with diaphragm 38 in the manner shown in FIG. 3. This action provides access to the contents of vial 12 in an aseptic manner. Furthermore, as a result of the fact that end 24 of the needle is blunt, and because diaphragm 38 constitutes an integral part of sealing piston 14, it has been found that the essentially invariable manner of rupture of diaphragm 38 is that the diaphragm stretches or balloons outwardly, breaks at one side of the diaphragm, and then rips about its periphery in such a manner that it folds away in an opening door type of motion into the configuration shown in FIG. 3, as needle end 24 advances. As a result of this, the flap formed by diaphragm 38 does not obstruct the lumen or bore of hollow needle 18, as may take place in many prior art structures. Also, the diaphragm rupture line is controlled and uniform, for greater assurance of sterility.

Ribs 39 act as a guide for entrance of connector 16 into vial 12.

Either before or after rupturing diaphragm 38, pointed end 20 of needle 18 can be advanced into an injection site 22 of a parenteral solution bag 40 or the like. A typical injection site 22 may comprise a tube 46, which is heat sealed, formed, or solvent sealed to bag 40 in such a manner that the bore of tube 46 is open for fluid flow. A latex plug or diaphragm 48 is placed in tube 46 to serve as a resealable injection site. Sleeve 30 is preferably proportioned so that the outer end of injection site 46 is adjacent the bottom 43 of sleeve 30, in position of use as shown in FIG. 3.

In accordance with this invention, needle end 20 can be advanced into bag 40 with a greater degree of penetration than would otherwise be possible in view of the presence of sleeve 30. The flat, heat-sealed flange 41 of a typical flexible bag 40 (such as a VIAFLEX bag) can fit into axial slots 34 of sleeve 30, as shown in FIGS. 3 and 4, to permit added penetration of needle end 20 into bag 40.

As seen in FIG. 3, needle end 20 can be positioned almost inside of bag 40 due to the interaction of the slots 34 of sleeve 30, flange 41 and bag walls 40.

Accordingly, when piston 14 is depressed toward the bottom of vial 12, the jet of liquid contents which is expelled out of needle end 20 is not slowed down by interaction with the narrow diameter of injection site 22, but passes immediately into the more spacious interior of bag 40. This materially improves the mixing characteristics of solutions, and particularly heavy additive solutions, with conventional parenteral solutions.

Accordingly, in the event that a nurse should forget to agitate the bag after addition of a heavy additive such as potassium chloride solution, the danger of infusing into the patient a concentrated aliquot of potassium chloride, retained in one end of the bag, is substantially reduced.

FIG. 4 shows how sleeve 30 can completely surround the injection site 22 and pass over flange or skirt 41 and move into contact with or close proximity to the walls of bag 40, for further advancement of needle end 20, while retaining the basic advantages of conventional, slot free sleeves described above.

Similar advantages of mixing, and the other advantages of this invention, can be obtained on use of the device of this invention in conjunction with rigid parenteral solution containers having projecting injection sites, and also in conjunction with injection sites of parenteral solution administration sets, and the like.

The above has been offered for illustrative purposes only, and is not to be considered as limiting the invention of this application, which is described in the claims below.

That which is claimed is:

1. A syringe connector assembly, in combination with a flat-edged container which carries a projecting tubular injection site extending through said flat edge, which assembly comprises:

a syringe connector, adapted for connection with a vial, said connector carrying a hollow injection needle with a forward pointed end, said needle passing through said projecting tubular injection site;

a substantially rigid sleeve having a first end mounted on said syringe connector and a second end extending axially beyond said forward needle end in spaced relation thereto, a pair of opposed, axial slots in said sleeve extending axially from said second end, said forward needle end extending at least beyond the inner end of said slots, said flat container edge being positioned within said axial slots and said injection site being positioned within said sleeve, whereby said forward end of the injection needle is sufficiently advanced through said injection site to be in direct communication with the interior of said container.

2. The syringe connector of claim 1 in which the outer end of said injection site is adjacent the end of said sleeve remote from said forward end of the injection needle.

* * * * *